(12) United States Patent
Kravitz et al.

(10) Patent No.: US 10,274,409 B2
(45) Date of Patent: Apr. 30, 2019

(54) VIBRATORY SENSOR AND METHOD OF VARYING VIBRATION IN A VIBRATORY SENSOR

(71) Applicant: Micro Motion, Inc., Boulder, CO (US)

(72) Inventors: Andrew S Kravitz, Erie, CO (US); Craig B McAnally, Thornton, CO (US)

(73) Assignee: Micro Motion, Inc., Boulder, CO (US)

( * ) Notice: Subject to any disclaimer, the term of this patent is extended or adjusted under 35 U.S.C. 154(b) by 241 days.

(21) Appl. No.: 14/782,135

(22) PCT Filed: May 31, 2013

(86) PCT No.: PCT/US2013/043568
§ 371 (c)(1),
(2) Date: Oct. 2, 2015

(87) PCT Pub. No.: WO2014/175902
PCT Pub. Date: Oct. 30, 2014

(65) Prior Publication Data
US 2016/0061708 A1    Mar. 3, 2016

Related U.S. Application Data

(60) Provisional application No. 61/816,221, filed on Apr. 26, 2013.

(51) Int. Cl.
*G01N 11/16* (2006.01)
*G01N 29/036* (2006.01)

(52) U.S. Cl.
CPC .......... *G01N 11/16* (2013.01); *G01N 29/036* (2013.01); *G01N 2291/02818* (2013.01)

(58) Field of Classification Search
CPC .. G01F 1/8422; G01F 23/2967; G01F 15/024; G01F 1/8413; G01F 1/8436;
(Continued)

(56) References Cited

U.S. PATENT DOCUMENTS

| 4,920,787 A | 5/1990 | Dual et al. |
| 5,339,258 A * | 8/1994 | Stabinger ............... G01N 9/002 702/50 |

(Continued)

FOREIGN PATENT DOCUMENTS

| JP | 2010-019694 A | 1/2010 |
| WO | 2006104485 A1 | 10/2006 |

*Primary Examiner* — Randy Gibson
*Assistant Examiner* — Gedeon M Kidanu
(74) *Attorney, Agent, or Firm* — The Ollila Law Group LLC

(57) ABSTRACT

A vibratory sensor (5) includes a vibratory element (104), a receiver circuit (134) that receives a vibration signal from the vibratory element (104), and a drive circuit (138) that generates a drive signal. The drive circuit (138) includes a closed-loop drive (143) and an open-loop drive (147). The meter electronics (20) vibrates the vibratory element (104) commencing at a commanded first frequency and in an open-loop manner to achieve a first target phase difference φ1 for a fluid being characterized and determines a corresponding first frequency point ω1, vibrates the vibratory element (104) commencing at a commanded second frequency and in the open-loop manner to achieve a second target phase difference φ2 and determines a corresponding second frequency point ω2, and determines a viscosity of the fluid being characterized using the first frequency point ω1 and the second frequency point ω2.

7 Claims, 7 Drawing Sheets

(58) Field of Classification Search
CPC .. G01F 1/8477; G01F 23/296; G01F 23/2966; G01N 9/002; G01N 11/16; G01N 2009/006
See application file for complete search history.

(56) References Cited

U.S. PATENT DOCUMENTS

| | | | | |
|---|---|---|---|---|
| 5,363,691 A * | 11/1994 | Gallagher | ............ | G01N 9/002 73/30.01 |
| 6,236,322 B1 * | 5/2001 | Lopatin | ............ | G01F 23/2967 340/612 |
| 2004/0078164 A1 * | 4/2004 | Lopatin | ............ | G01F 23/2967 702/100 |
| 2005/0052813 A1 * | 3/2005 | Kobayashi | ............ | G01G 3/16 361/143 |
| 2006/0131994 A1 * | 6/2006 | D'Angelico | ........ | G01F 23/2967 310/317 |
| 2008/0252283 A1 * | 10/2008 | McAnally | ............ | G01F 1/8413 324/76.78 |
| 2009/0205411 A1 * | 8/2009 | Muller | ................ | G01F 23/2967 73/64.53 |
| 2010/0005865 A1 * | 1/2010 | Miura | .................... | G01N 11/16 73/54.41 |
| 2010/0083750 A1 * | 4/2010 | D'Angelico | ........ | G01F 23/2967 73/290 V |
| 2010/0083752 A1 * | 4/2010 | Malinek | ................ | G01F 23/296 73/32 R |
| 2010/0161251 A1 * | 6/2010 | D'Angelico | ........ | G01F 23/2967 702/54 |
| 2010/0198531 A1 * | 8/2010 | Bell | ......................... | G01F 1/74 702/45 |
| 2011/0098945 A1 * | 4/2011 | McAnally | ............ | G01F 1/8436 702/48 |
| 2011/0264385 A1 * | 10/2011 | Weinstein | ............ | G01F 1/8436 702/48 |

* cited by examiner

VIBRATORY SENSOR AND METHOD OF VARYING VIBRATION IN A VIBRATORY SENSOR

BACKGROUND OF THE INVENTION

1. Field of the Invention

The present invention relates to a vibratory sensor and method of varying vibration in a vibratory sensor.

2. Statement of the Problem

Vibratory sensors, such as vibratory densitometers and vibratory viscometers, operate by detecting motion of a vibrating element that vibrates in the presence of a fluid to be characterized. Properties associated with the fluid, such as density, viscosity, temperature and the like, can be determined by processing a vibration signal or signals received from one or more motion transducers associated with the vibrating element. The vibration of the vibrating element is generally affected by the combined mass, stiffness and damping characteristics of the vibrating element in combination with the fluid.

The viscosity of a fluid can be measured by generating vibration responses at frequencies $\omega 1$ and $\omega 2$ that are above and below a resonant frequency $\omega 0$ of the combined fluid and vibratory sensor. At the resonance frequency $\omega 0$, the phase difference $\phi 0$ may be about 90 degrees. The two frequency points $\omega 1$ and $\omega 2$ are defined as the drive frequencies where the drive signal phase and the vibration signal phase differ by the phase differences $\phi 1$ and $\phi 2$, respectively. The phase difference $\phi 1$ may be defined as the point where the phase difference between the drive signal phase and the vibration signal phase is about 135 degrees. The phase difference $\omega 2$ may be defined as the point where the phase difference between the drive signal phase and the vibration signal phase is about 45 degrees.

The distance between these two frequency points $\omega 1$ and $\omega 2$ (i.e., the difference in frequency between $\omega 1$ and $\omega 2$) is used to determine the term Q, which is proportional to viscosity and can be approximated by the formula:

$$\text{viscosity} \approx Q = \omega 0/(\omega 2 - \omega 1) \quad (1)$$

The resonant frequency $\omega 0$ is centered between the two frequency points $\omega 1$ and $\omega 2$. Therefore, the resonant frequency $\omega 0$ can be defined as:

$$\omega 0 \approx 0.5*(\omega 2 + \omega 1) \quad (2)$$

The frequency points $\omega 1$ and $\omega 2$ are determined during operation when the sensor element interacts with the fluid to be characterized. In order to properly determine the frequency points $\omega 1$ and $\omega 2$, the prior art drive system uses a closed loop drive, driving the sensor element to alternate between the two phase difference points ($\phi 1$ and $\phi 2$) and recording the vibration frequencies $\omega 1$ and $\omega 2$ at these points. By using a closed-loop drive, the prior art drive system ensures that the phase difference measurement is stable when the vibration frequencies $\omega 1$ and $\omega 2$ are determined.

Alternatively, the frequency points $\omega 1$ and $\omega 2$ are defined as half-power points, as they comprise frequency points where the power in the vibration signal has half the power of the resonant frequency $\omega 0$, or where the half-power point amplitude $A_{half}$ is ($A_{half} = A_0/\sqrt{2}$). The $A_0$ term is the amplitude of the vibration signal at the resonant frequency $\omega 0$. The two frequency points $\omega 1$ and $\omega 2$ are also known as 3 dB points, where the vibration signal power is 3 dB down from the resonant frequency power.

FIG. 1 shows a prior art vibratory sensor comprising a vibratory sensor element and a signal processor coupled to the sensor element. The prior art vibratory sensor includes a driver for vibrating a sensor element and a pickoff sensor that creates a vibration signal in response to the vibration. The vibration signal is sinusoidal in nature. The signal processor receives the vibration signal and processes the vibration signal to generate one or more fluid characteristics or fluid measurements. The signal processor determines both the frequency and the amplitude of the vibration signal. The frequency and amplitude of the vibration signal can be further processed to determine a density of the fluid, or can be processed to determined additional or other fluid characteristics, such as the viscosity.

The prior art signal processor generates a drive signal for the driver using a closed-loop drive circuit. The drive signal typically is based on the received vibration signal, wherein the prior art closed-loop drive circuit processes the received vibration signal to create the drive signal. The drive signal may be based on the frequency and amplitude of the received vibration signal, wherein the received vibration signal comprises feedback that enables the prior art drive system to achieve a target vibration. The prior art vibratory sensor drives the sensor element using the closed-loop drive and using a feedback element, wherein the closed-loop drive incrementally changes the drive frequency and monitors the feedback element until the desired target point is reached. The desired endpoint comprises a phase difference ($\phi$) between the drive signal and the resulting pickoff signal achieving the phase difference $\phi 1$ or the phase difference $\phi 2$.

FIG. 2 is a flow chart of a method of operation of the prior art vibratory sensor for measuring fluid viscosity. Steps 1-4 below determine the frequency of the first frequency point $\omega 1$ while steps 5-8 determine the frequency of the second frequency point $\omega 2$.

In step 1, a vibration setpoint is set to a first target phase difference $\phi 1$ and the sensor element is vibrated from the current vibration frequency. The first target phase difference $\phi 1$ is achieved by varying the frequency of the drive signal, starting from the current vibration frequency. The current vibration frequency is gradually changed in a closed-loop manner and according to received feedback, such as feedback regarding the difference between a current phase difference and the target phase difference. The vibration frequency is incrementally ramped up or down from the current vibration frequency, depending on whether the phase difference is to be increased or decreased.

In step 2, the current phase difference is compared to the first target phase difference $\phi 1$. If the first target phase difference $\phi 1$ has been achieved, then the method proceeds to step 4. Otherwise, the method branches to step 3 until the first target phase difference $\phi 1$ is achieved.

In step 3, a wait is performed. Consequently, the method loops and waits until the vibration setpoint has been achieved. The prior art vibratory sensor therefore waits for the actual vibration of the sensor element to reach the vibration setpoint. Due to the closedloop drive operation, the sensor element does not achieve vibration at the vibration setpoint until at least a known wait time has elapsed.

The wait may be for a fixed predetermined time or may vary in length. Environmental conditions may require a longer than expected time to achieve the target phase difference. The length of the wait may depend on various factors. The length of the wait may depend on a distance to the target phase difference from the initial phase difference. The length of the wait may depend on the physical characteristics of the sensor element. The length of the wait may depend on the nature of the fluid being measured (including the density and/or viscosity of the fluid). The length of the wait may depend on the power available to the prior art vibratory sensor.

In step 4, where the vibration setpoint has been achieved and the phase difference between the drive sensor signal and the pickoff sensor signal corresponds to the first phase difference $\phi 1$, then the corresponding first vibration frequency $\omega 1$ is recorded. The first frequency point $\omega 1$ comprises the vibration frequency that generates the first target phase difference $\phi 1$. The first vibration frequency $\omega 1$ may comprise the frequency where the phase difference between the drive signal phase and the pickoff signal phase is about 135 degrees, for example.

In step 5, the vibration setpoint is set to a second target phase difference $\phi 2$ and the sensor element is vibrated from the current vibration frequency. The second target phase difference $\phi 2$ is achieved by varying the frequency of the drive signal, starting from the current vibration frequency. The current vibration frequency is gradually changed in a closed-loop manner and according to received feedback, such as feedback regarding the difference between a current phase difference and the target phase difference. The vibration frequency is incrementally ramped up or down from the current vibration frequency, depending on whether the phase difference is to be increased or decreased. It should be understood that the starting vibration frequency is therefore the current vibration frequency, which comprises the vibration frequency obtained in step 4 above.

In step 6, the current phase difference is compared to the second target phase difference $\phi 2$. If the second target phase difference $\phi 2$ has been achieved, then the method proceeds to step 8. Otherwise, the method branches to step 7 until the second target phase difference $\phi 2$ is achieved.

In step 7, a wait is performed. Consequently, the method loops and waits until the vibration setpoint has been achieved. Due to the closedloop drive operation, the sensor element does not achieve vibration at the vibration setpoint until at least a known wait time has elapsed, as previously discussed.

In step 8, where the vibration setpoint has been achieved and the phase difference between the drive sensor signal and the pickoff sensor signal corresponds to the second phase difference $\phi 2$, then the corresponding second frequency point $\omega 2$ is recorded. The second frequency point $\omega 2$ comprises the vibration frequency that generates the second target phase difference $\phi 2$. The second frequency point $\omega 2$ may comprise the frequency where the phase difference between the drive signal phase and the pickoff signal phase is about 45 degrees, for example.

FIG. 3 is a graph of a closed-loop vibration response of the prior art vibratory sensor of FIG. 1. The vertical axis represents vibration frequency ($\omega$) and the horizontal axis represents time (t). It can be seen that the prior art vibratory sensor is alternatingly vibrated at the first frequency point $\omega 1$ and then at the second frequency point $\omega 2$, wherein this pattern is iteratively repeated. It should be understood that the first and second frequency points $\omega 1$ and $\omega 2$ are not necessarily constant. The first and second vibration frequencies $\omega 1$ and $\omega 2$ may change due to changes in the fluid being characterized by the vibratory sensor, for example.

Due to the closed-loop design of the drive portion of the prior art vibratory sensor, it can be seen that the actual vibration frequency changes smoothly and continuously, but slowly. Each change in drive frequency requires a closed-loop time period $T_{CL}$ to accomplish, due to the feedback used to achieve the target phase difference. As a result, the prior art vibratory tine sensor cannot measure rapid changes in $\omega 1$ and $\omega 2$, and therefore cannot measure rapid changes in viscosity of the fluid to be characterized. Further, even where the time period $T_{CL}$ is small, it can be seen that the time period $T_{CL}$ is repeated and will therefore add up and will affect the operation of the prior art vibratory sensor.

Aspects of the Invention

In one aspect of the invention, a vibratory sensor comprises:
  a vibratory element configured to generate a vibration signal; and
  a receiver circuit that receives the vibration signal from the vibratory element; and
  a drive circuit coupled to the receiver circuit and the vibratory element and generating a drive signal that vibrates the vibratory element, wherein the drive circuit vibrates the vibratory element commencing at a commanded first frequency and in an open-loop manner to achieve a first target phase difference $\phi 1$ for a fluid being characterized and determines a corresponding first frequency point $\omega 1$, vibrates the vibratory element commencing at a commanded second frequency and in the open-loop manner to achieve a second target phase difference $\phi 2$ and determines a corresponding second frequency point $\omega 2$, and determines a viscosity of the fluid being characterized using the first frequency point $\omega 1$ and the second frequency point $\omega 2$.

Preferably, the vibratory sensor iteratively performs the vibrating and determining steps.

Preferably, the commanded first frequency comprises a previous-time first frequency point $\omega 1_{time=(t-1)}$ and the commanded second frequency comprises a previous-time second frequency point $\omega 2_{time=(t-1)}$.

Preferably, the drive circuit comprises a closed-loop drive that generates the drive signal to achieve a target phase difference and commencing at a current vibration frequency and an open-loop drive that generates the drive signal to achieve a target phase difference and commencing at a commanded first or second frequency.

Preferably, vibrating the vibratory element of the vibratory sensor in the open-loop manner comprises the drive circuit setting a vibration setpoint to the first target phase difference $\phi 1$, the drive circuit vibrating the vibratory element in the open-loop manner and at the commanded first frequency, the drive circuit comparing a current first phase difference to the first target phase difference $\phi 1$ and waiting until the current first phase difference is substantially equal to the first target phase difference $\phi 1$, if the current first phase difference is equal to the first target phase difference $\phi 1$, then the drive circuit recording the corresponding first frequency point $\omega 1$, wherein achieving the first target phase difference $\phi 1$ generates the first frequency point $\omega 1$ in the vibratory element, the drive circuit setting the vibration setpoint to the second target phase difference $\phi 2$, the drive circuit vibrating the vibratory element in the open-loop manner and at the commanded second frequency, the drive circuit comparing a current second phase difference to the second target phase difference $\phi 2$ and waiting until the current second phase difference is substantially equal to the second target phase difference $\phi 2$, and if the current second phase difference is equal to the second target phase difference $\phi 2$, then the drive circuit recording the corresponding second frequency point $\omega 2$, wherein achieving the second target phase difference $\phi 2$ generates the second frequency point $\omega 2$ in the vibratory element.

Preferably, the drive circuit is further configured to vibrate the vibratory element in a closed-loop manner to achieve the first target phase difference $\phi 1$ for the fluid being characterized and determining a corresponding first frequency point $\omega 1$, with the vibrating commencing at the current vibration frequency, and vibrate the vibratory element in the closed-loop manner to achieve the second target phase difference $\phi 2$ for the fluid being characterized and determining a corresponding second frequency point $\omega 2$, with the vibrating commencing at the current vibration frequency.

Preferably, the drive circuit selects the open-loop operation if the fluid being characterized is substantially stable.

Preferably, the drive circuit is further configured to vibrate the vibratory element commencing at the commanded first frequency and in the open-loop manner to approximate the first target phase difference $\phi 1$ for a fluid being characterized, vibrate the vibratory element in a closed-loop manner to achieve the first target phase difference $\phi 1$ and determine a corresponding first frequency point $\omega 1$, vibrate the vibratory element commencing at the commanded second frequency and in the open-loop manner to approximate the second target phase difference $\phi 2$ for the fluid being characterized, vibrate the vibratory element in the closed-loop manner to achieve the second target phase difference $\phi 2$ and determine a corresponding second frequency point $\omega 2$, and determine a viscosity of the fluid being characterized using the first frequency point $\omega 1$ and the second frequency point $\omega 2$.

Preferably, the receiver circuit is coupled to the drive circuit, with the receiver circuit providing the vibration signal amplitude and the vibration signal frequency to the drive circuit, with the drive circuit generating a drive signal for the vibratory element using the vibration signal amplitude and the vibration signal frequency.

Preferably, the vibratory sensor comprises a vibratory tine sensor and with the vibratory element comprising a tuning fork structure.

In one aspect of the invention, a method of varying vibration in a vibratory sensor comprises:

vibrating a vibratory element of a vibratory sensor commencing at a commanded first frequency and in an open-loop manner to achieve a first target phase difference $\phi 1$ for a fluid being characterized and determining a corresponding first frequency point $\omega 1$;

vibrating the vibratory element commencing at a commanded second frequency and in the open-loop manner to achieve a second target phase difference $\phi 2$ and determining a corresponding second frequency point $\omega 2$; and determining a viscosity of the fluid being characterized using the first frequency point $\omega 1$ and the second frequency point $\omega 2$.

Preferably, the method iteratively performs the vibrating and determining steps.

Preferably, the commanded first frequency comprises a previous-time first frequency point $\omega 1_{time=(t-1)}$ and the commanded second frequency comprises a previous-time second frequency point $\omega 2_{time=(t-1)}$.

Preferably, vibrating the vibratory element in the open-loop manner comprises setting a vibration setpoint to the first target phase difference $\phi 1$, vibrating the vibratory element in the open-loop manner and at the commanded first frequency, comparing a current first phase difference to the first target phase difference $\phi 1$ and waiting until the current first phase difference is substantially equal to the first target phase difference $\phi 1$, if the current first phase difference is equal to the first target phase difference $\phi 1$, then recording the corresponding first frequency point $\omega 1$, wherein achieving the first target phase difference $\phi 1$ generates the first frequency point $\omega 1$ in the vibratory element, setting the vibration setpoint to the second target phase difference $\phi 2$, vibrating the vibratory element in the open-loop manner and at the commanded second frequency, comparing a current second phase difference to the second target phase difference $\phi 2$ and waiting until the current second phase difference is substantially equal to the second target phase difference $\phi 2$, and if the current second phase difference is equal to the second target phase difference $\phi 2$, then recording the corresponding second frequency point $\omega 2$, wherein achieving the second target phase difference $\phi 2$ generates the second frequency point $\omega 2$ in the vibratory element.

Preferably, the method further comprises the preliminary steps of vibrating the vibratory element in a closed-loop manner to achieve the first target phase difference $\phi 1$ for the fluid being characterized and determining a corresponding first frequency point $\omega 1$, with the vibrating commencing at the current vibration frequency, and vibrating the vibratory element in the closed-loop manner to achieve the second target phase difference $\phi 2$ for the fluid being characterized and determining a corresponding second frequency point $\omega 2$, with the vibrating commencing at the current vibration frequency.

Preferably, the method selects the open-loop operation if the fluid being characterized is substantially stable.

Preferably, the method comprises vibrating the vibratory element commencing at the commanded first frequency and in the open-loop manner to approximate the first target phase difference $\phi 1$ for a fluid being characterized, vibrating the vibratory element in a closed-loop manner to achieve the first target phase difference $\phi 1$ and determining a corresponding first frequency point $\omega 1$, vibrating the vibratory element commencing at the commanded second frequency and in the open-loop manner to approximate the second target phase difference $\phi 2$ for the fluid being characterized, vibrating the vibratory element in the closed-loop manner to achieve the second target phase difference $\phi 2$ and determining a corresponding second frequency point $\omega 2$, and determining a viscosity of the fluid being characterized using the first frequency point $\omega 1$ and the second frequency point $\omega 2$.

Preferably, the vibratory sensor comprises a vibratory tine sensor and with the vibratory element comprising a tuning fork structure.

DESCRIPTION OF THE DRAWINGS

The same reference number represents the same element on all drawings. The drawings are not necessarily to scale.

DETAILED DESCRIPTION OF THE INVENTION

FIGS. 4-7 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
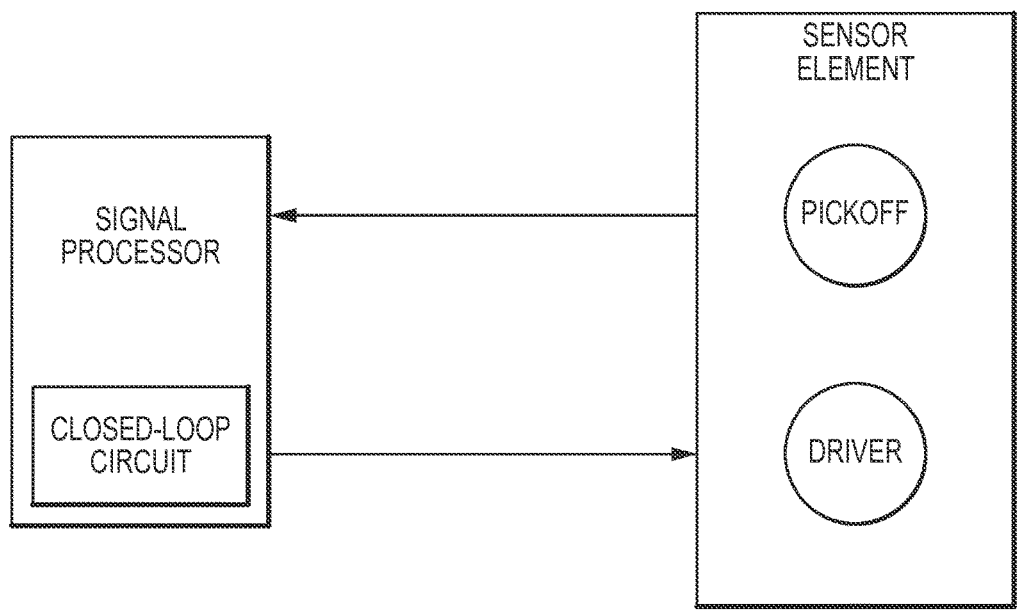
FIG. 1 shows a prior art vibratory sensor comprising a vibratory sensor element and a signal processor coupled to the sensor element comprising a vibratory sensor element and a signal processor coupled to the sensor element.
Figure 2:
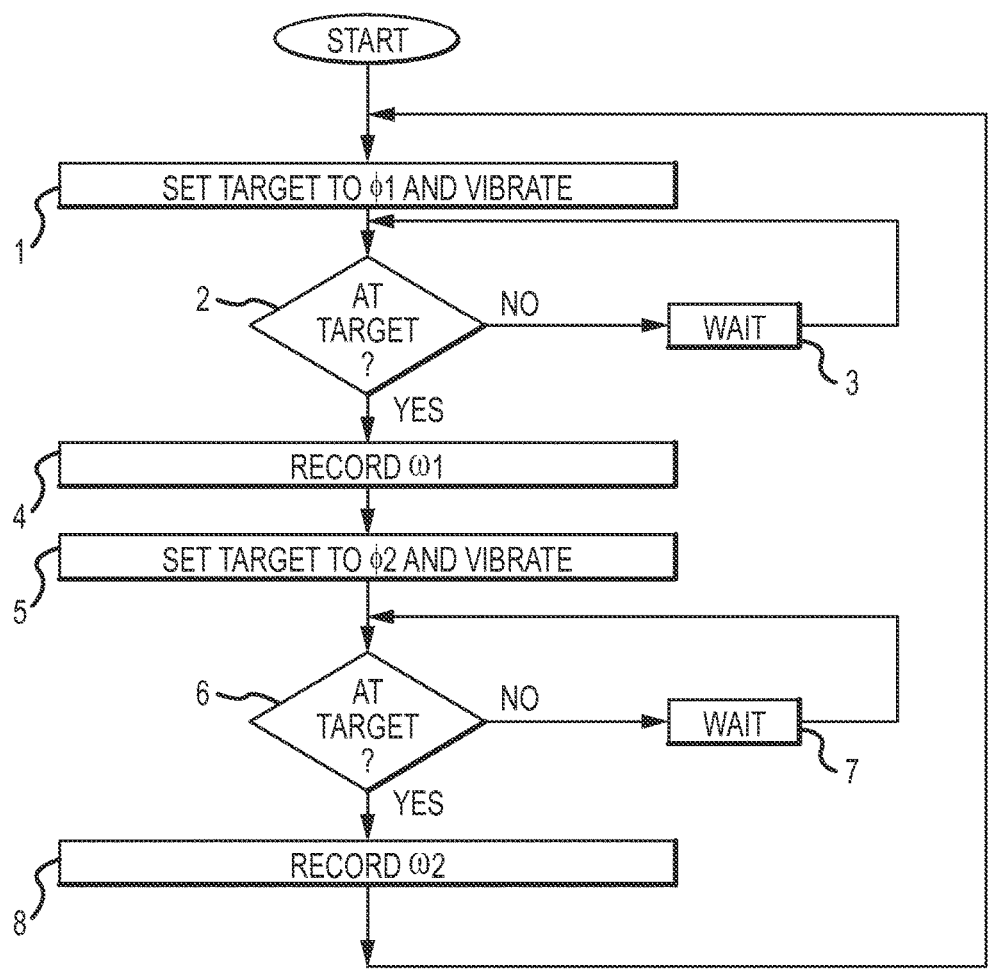
FIG. 2 is a flow chart of a method of operation of the prior art vibratory sensor for measuring fluid viscosity.
Figure 3:
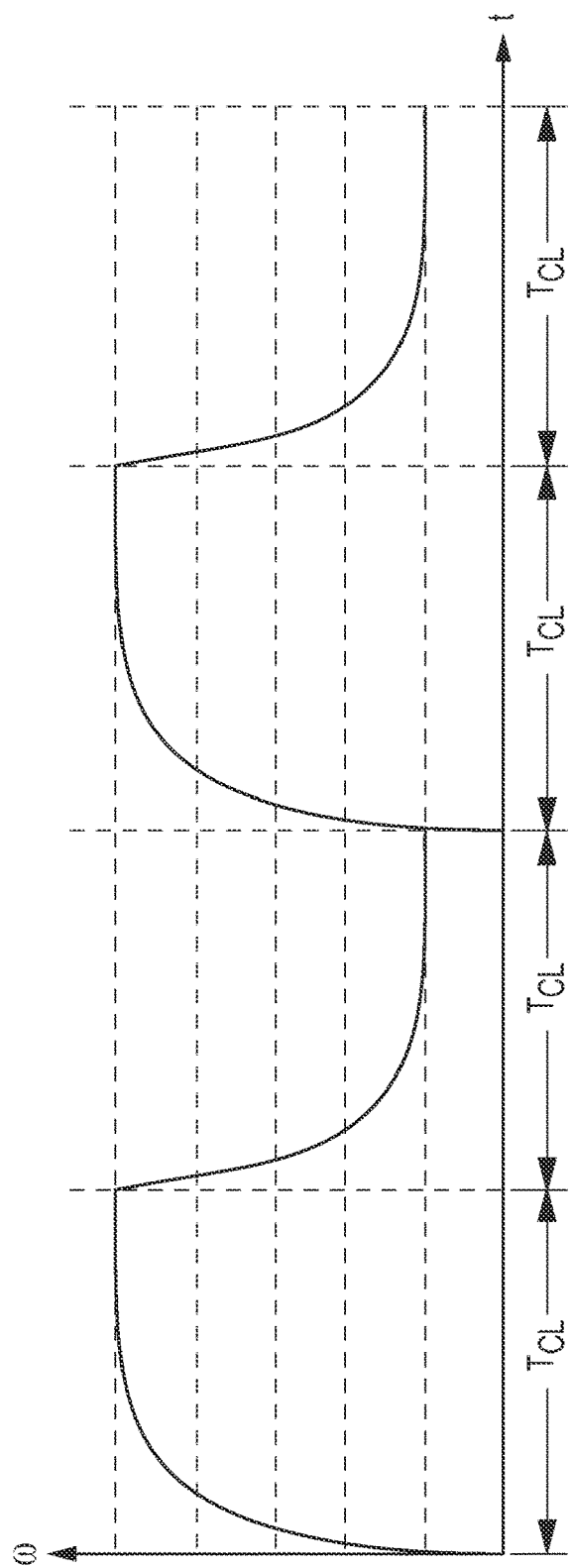
FIG. 3 is a graph of a closed-loop vibration response of the prior art vibratory sensor of FIG. 1.
Figure 4:
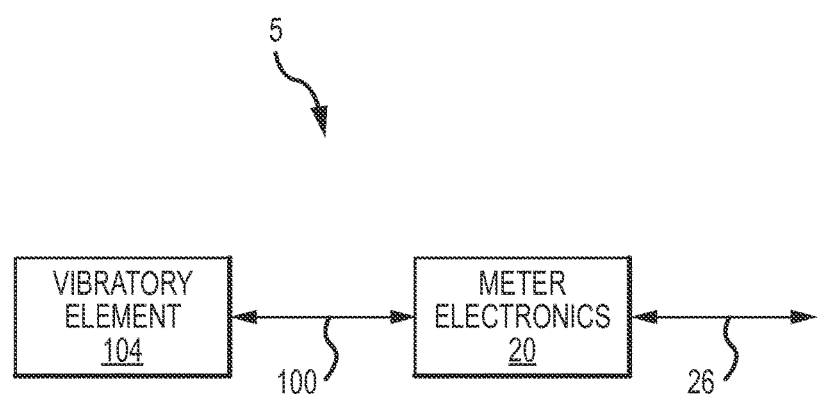
FIG. 4 shows a vibratory sensor according to an embodiment of the invention.

FIG. 4 shows a vibratory sensor 5 according to an embodiment of the invention. The vibratory sensor 5 may comprise a vibratory element 104 and meter electronics 20, wherein the vibratory element 104 is coupled to the meter electronics 20 by a lead or leads 100. In some embodiments, the vibratory sensor 5 may comprise a vibratory tine sensor or fork density sensor (see FIG. 5 and the accompanying discussion). However, other vibratory sensors are contemplated and are within the scope of the description and claims.

The vibratory sensor 5 may be at least partially immersed into a fluid to be characterized. For example, the vibratory sensor 5 may be mounted in a pipe or conduit. The vibratory sensor 5 may be mounted in a tank or container or structure for holding a fluid. The vibratory sensor 5 may be mounted in a manifold or similar structure for directing a fluid flow. Other mounting arrangements are contemplated, however, and are within the scope of the description and claims.

The fluid can comprise a liquid. The fluid can comprise a gas. Alternatively, the fluid can comprise a multi-phase fluid, such as a liquid that includes entrained gas, entrained solids, multiple liquids, or combinations thereof.

The vibratory sensor 5 may operate to provide fluid measurements. The vibratory sensor 5 may provide fluid measurements including one or more of a fluid density and a fluid viscosity for a fluid, including flowing or non-flowing fluids. The vibratory sensor 5 may provide fluid measurements including a fluid mass flow rate, a fluid volume flow rate, and/or a fluid temperature. This listing is not exhaustive and the vibratory sensor 5 may measure or determine other fluid characteristics.

The meter electronics 20 may provide electrical power to the vibratory element 104 via the lead or leads 100. The meter electronics 20 may control operation of the vibratory element 104 via the lead or leads 100. For example, the meter electronics 20 may generate a drive signal and supply the drive signal to the vibratory element 104, wherein the vibratory element 104 generates a vibration in one or more vibratory components using the drive signal. The drive signal may control the vibrational amplitude. The drive signal may control the vibrational frequency. The drive signal may control the vibrational duration and/or vibrational timing.

The meter electronics 20 may receive a vibration signal or signals from the vibratory element 104 via the lead or leads 100. The meter electronics 20 may process the vibration signal or signals in order to generate a density measurement, for example. It should be understood that other or additional measurements may be generated from the vibration signal or signals.

The meter electronics 20 may process the vibration signal or signals received from the vibratory element 104 to determine a frequency of the signal or signals. The frequency may comprise a resonant frequency of the fluid. The resonant frequency may be used to determine a density of the fluid. Further, or in addition, the meter electronics may process the vibration signal or signals to determine other characteristics of the fluid, such as a viscosity or a phase shift between signals that can be processed to determine a fluid flow rate, for example. Other vibrational response characteristics and/or fluid measurements are contemplated and are within the scope of the description and claims.

The meter electronics 20 may be further coupled to a communication link 26. The meter electronics 20 may communicate a vibration signal over the communication link 26. The meter electronics 20 may process the received vibration signal to generate a measurement value or values and may communicate a measurement value or values over the communication link 26.

In addition, the meter electronics 20 may receive information over the communication link 26. The meter electronics 20 may receive commands, updates, operational values or operational value changes, and/or programming updates or changes over the communication link 26.

Figure 5:
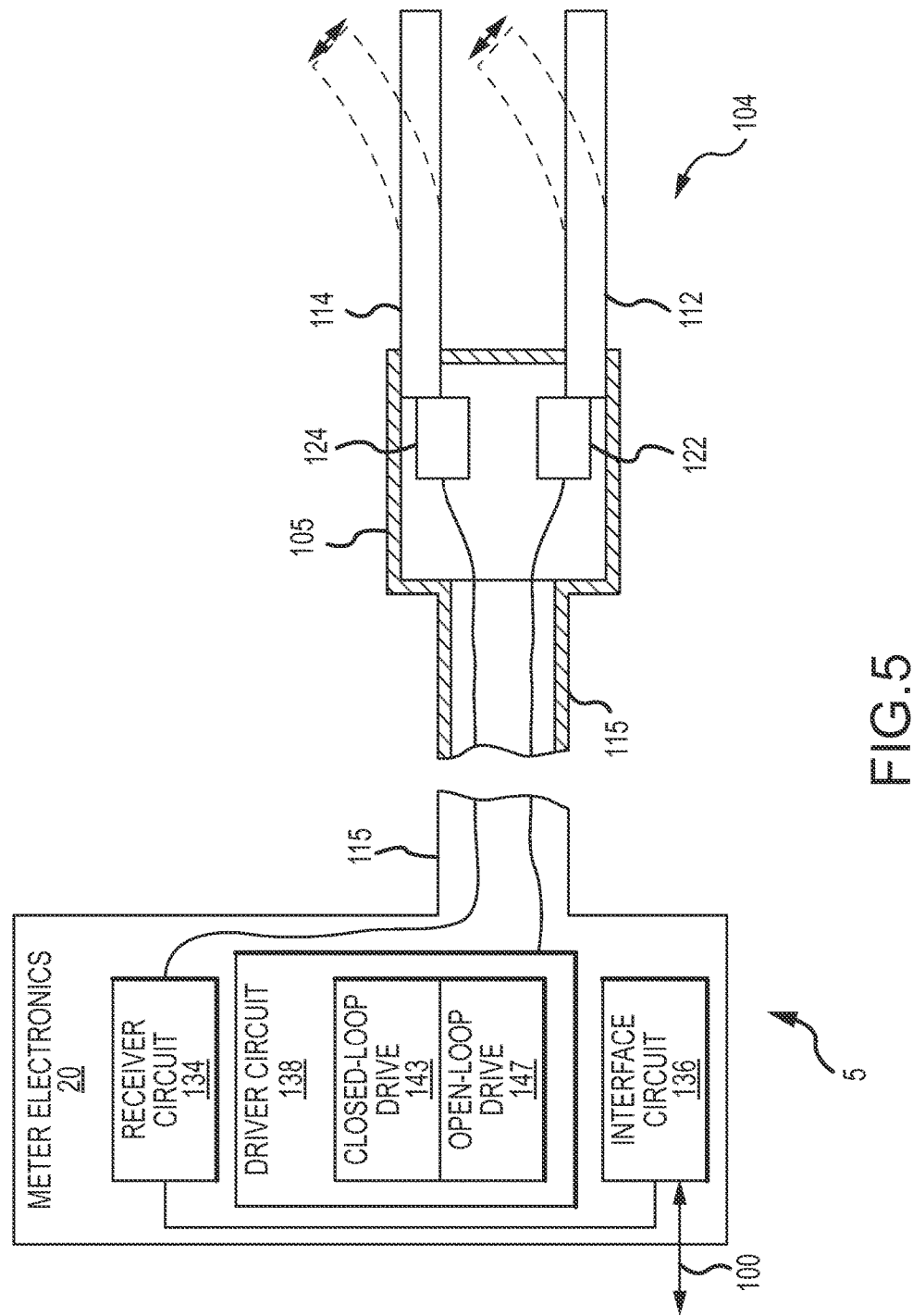
FIG. 5 shows the vibratory sensor according to an embodiment of the invention.

FIG. 5 shows the vibratory sensor 5 according to an embodiment of the invention. The vibratory sensor 5 in the embodiment shown comprises a vibratory tine sensor 5, including meter electronics 20 coupled to the vibratory element 104 by a shaft 115 in the embodiment shown. The shaft 115 may be of any desired length. The shaft 115 may be at least partially hollow and wires or other conductors may extend between the meter electronics 20 and the vibratory element 104 through the shaft 115.

The meter electronics 20 may include circuit components such as a receiver circuit 134, a drive circuit 138, and an interface circuit 136 in the embodiment shown.

In the embodiment shown, the receiver circuit 134 and the drive circuit 138 are directly coupled to the leads of the vibratory element 104 in the embodiment shown. Alternatively, the meter electronics 20 may comprise a separate component or device from the vibratory element 104, wherein the receiver circuit 134 and the drive circuit 138 are coupled to the vibratory element 104 via the lead or leads 100, as shown in FIG. 4.

The vibratory element 104 of the vibratory sensor 5 in the embodiment shown comprises a tuning fork structure 104, wherein the vibratory element 104 is at least partially immersed in the fluid being measured. The vibratory element 104 includes a housing 105 that may be affixed to another structure, such as a pipe, conduit, tank, receptacle, manifold, or any other fluid-handling structure. The housing 105 retains the vibratory element 104, while the vibratory element 104 remains at least partially exposed. The vibratory element 104 therefore is configured to be immersed in the fluid.

The vibratory element 104 in the embodiment shown includes first and second tines 112 and 114 that are configured to extend at least partially into the fluid. The first and second tines 112 and 114 comprise elongate elements that may have any desired cross-sectional shape. The first and second tines 112 and 114 may be at least partially flexible or resilient in nature.

The vibratory sensor 5 further includes corresponding first and second piezo elements 122 and 124 that comprise piezo-electric crystal elements. The first and second piezo elements 122 and 124 are located adjacent to the first and second tines 112 and 114, respectively. The first and second piezo elements 122 and 124 are configured to contact and mechanically interact with the first and second tines 112 and 114.

The first piezo element 122 may contact at least a portion of the first tine 112. The first piezo element 122 may be electrically coupled to the drive circuit 138, with the drive circuit 138 providing a time-varying drive signal to the first piezo element 122. The first piezo element 122 may expand and contract when subjected to the time-varying drive signal. As a result, the first piezo element 122 may alternatingly deform and displace the first tine 112 from side to side in a vibratory motion (see dashed lines), disturbing the fluid in a periodic, reciprocating manner.

The second piezo element 124 may be coupled to a receiver circuit 134 that produces a time-varying vibration response signal corresponding to the deformations of the second tine 114 in the fluid. Movement of the second tine 114 may therefore cause a corresponding electrical vibration signal to be generated by the second piezo element 124. The second piezo element 124 transmits the vibration signal to the meter electronics 20. The meter electronics 20 processes the vibration signal and may measure the vibration signal amplitude and/or the vibration signal frequency of the vibration signal.

The meter electronics 20 may include the interface circuit 136. The interface circuit 136 may be configured to communicate with external devices. The interface circuit 136 may communicate a vibration measurement signal or signals and may communicate determined fluid characteristics to one or more external devices. The meter electronics 20 may transmit vibration signal characteristics via the interface circuit 136, such as a vibration signal frequency and/or a vibration signal amplitude of the vibration signal. The meter electronics 20 may transmit fluid measurements via the interface circuit 136, such as a density and/or viscosity of the fluid, among other things. Other fluid measurements are contemplated and are within the scope of the description and claims. In addition, the interface circuit 136 may receive communications from external devices, including commands and data for generating measurement values, for example.

In some embodiments, the receiver circuit 134 is coupled to the drive circuit 138, with the receiver circuit 134 providing the vibration signal amplitude and the vibration signal frequency to the drive circuit 138, with the drive circuit 138 generating a drive signal for the vibratory element 104 using the vibration signal amplitude and the vibration signal frequency.

The drive circuit 138 may receive the vibration signal and may generate a drive signal from the vibration signal, and may modify characteristics of the vibration signal in order to generate the drive signal. The vibratory element 104 is generally maintained at a resonant frequency, as influenced by the surrounding fluid. The vibratory element 104 is typically maintained at the resonant frequency by the drive circuit 138. The drive circuit 138 may modify the vibration signal to produce a desired vibrational disturbance in the fluid. The drive circuit 138 further may modify the vibration signal to compensate for the length of the leads between the meter electronics 20 and the vibratory element 104 and/or to compensate for other losses in the vibration signal, for example.

The drive circuit 138 may include a closed-loop drive 143 and an open-loop drive 147. Either one of the closed-loop drive 143 or the open-loop drive 147 may be used by the drive circuit 138 to generate a drive signal and supply the drive signal to the vibratory element 104 (i.e., to the first piezo element 122).

The closed-loop drive 143 generates a closed-loop drive signal, wherein the closed-loop drive 143 uses the vibration signal received from the vibratory element 104 (i.e., from the second piezo element 124) to generate the drive signal. The closed-loop drive 143 therefore operates based on feedback and a feedback algorithm. The feedback comprises a difference between the current vibration and the commanded vibration target. The drive signal is smoothly and continuously varied by the closed-loop drive 143 until the vibration signal (i.e., the feedback) reaches the vibration target. Therefore, if a first frequency point $\omega 1$ is commanded, the closed-loop drive 143 will incrementally change from a current vibration frequency of $\omega 2$ until the target vibration of $\omega 1$ is eventually achieved.

In some embodiments, the drive circuit 138 comprises a closed-loop drive 143 that generates the drive signal to achieve a target phase difference, commencing at a current vibration frequency, and an open-loop drive 147 that generates the drive signal to achieve a target phase difference, commencing at a commanded vibration frequency.

The open-loop drive 147 is configured to generate a drive signal based on a commanded vibration target. Therefore, if a first vibration frequency is commanded, the open-loop drive 147 will generate a drive signal at the first vibration frequency, even where the drive circuit 138 had been vibrating the vibratory element 104 at the second vibration frequency. The open-loop drive 147 does not operate based on feedback and the open-loop drive 147 therefore can immediately vibrate at a commanded vibration target.

In some embodiments, the drive circuit 138 vibrates the vibratory element 104 commencing at a commanded first frequency and in an open-loop manner to achieve a first target phase difference $\phi 1$ for a fluid being characterized and determines a corresponding first frequency point $\omega 1$, vibrates the vibratory element 104 commencing at a commanded second frequency and in the open-loop manner to achieve a second target phase difference $\phi 2$ and determines a corresponding second frequency point $\omega 2$, and determines a viscosity of the fluid being characterized using the first frequency point $\omega 1$ and the second frequency point $\omega 2$.

It should be understood that the commanded first and second frequencies are only approximations of the first and second frequency points $\omega 1$ and $\omega 2$. The commanded first and second frequencies may not be exactly the final values of the actual first and second frequency points $\omega 1$ and $\omega 2$, such as where the density of the fluid is varying over time.

In some embodiments, vibrating the vibratory element 104 of the vibratory sensor 5 in the open-loop manner comprises the drive circuit 138 setting a vibration setpoint to the first target phase difference $\phi 1$, the drive circuit 138 vibrating the vibratory element 104 commencing at the commanded first frequency and in the open-loop manner, the drive circuit 138 comparing a current first phase difference to the first target phase difference $\phi 1$ and waiting until the current first phase difference is substantially equal to the first target phase difference $\phi 1$, if the current first phase difference is equal to the first target phase difference $\phi 1$, then the drive circuit 138 recording the corresponding first frequency point $\omega 1$, wherein achieving the first target phase difference $\phi 1$ generates the first frequency point $\omega 1$ in the vibratory element 104, the drive circuit 138 setting the vibration setpoint to the second target phase difference $\phi 2$, the drive circuit 138 vibrating the vibratory element 104 commencing at the commanded second frequency and in the open-loop manner, the drive circuit 138 comparing a current second phase difference to the second target phase difference φ2 and waiting until the current second phase difference is substantially equal to the second target phase difference φ2, and if the current second phase difference is equal to the second target phase difference φ2, then the drive circuit 138 recording the corresponding second frequency point ω2, wherein achieving the second target phase difference φ2 generates the second frequency point ω2 in the vibratory element 104.

In some embodiments, the drive circuit 138 is configured to vibrate the vibratory element 104 commencing at a commanded first frequency and in the open-loop manner to approximate a first target phase difference φ1 for a fluid being characterized, vibrate the vibratory element 104 in a closed-loop manner to achieve the first target phase difference φ1 and determining a corresponding first frequency point ω1, vibrate the vibratory element 104 commencing at a commanded second frequency and in the open-loop manner to approximate a second target phase difference φ2 for the fluid being characterized, vibrate the vibratory element 104 in the closed-loop manner to achieve the second target phase difference φ2 and determining a corresponding second frequency point ω2, and determine a viscosity of the fluid being characterized using the first frequency point ω1 and the second frequency point ω2.

An open-loop controller, which may also be called a non-feedback controller, computes its input into a system using only a current state of the system and a model of the system. A characteristic of the open-loop controller is that it does not use feedback to determine if the output has achieved the desired goal of the input. This means that the system does not observe the output of the processes that it is controlling. Consequently, a true open-loop system cannot correct errors in the desired and achieved values. It also may not compensate for disturbances in the system. However, an advanced open-loop system can be used, wherein the control methodology can be self-learning and adaptive. As a result, the vibratory sensor according to any of the embodiments can employ either a traditional open-loop control process or can employ an adaptive open-loop control process, wherein some feedback or outside values are used to ensure that the actual phase difference between the drive signal phase and the vibration signal phase approximates or closely approaches the target phase difference.

The drive circuit 138 forces the vibratory element 104 to a vibration frequency that is near to the desired vibration frequency by driving it with an open-loop drive signal to vibrate at the last measured value of the frequency point. For instance, by driving a sensor at ω1, with the frequency obtained from the last measured value of ω1 (referred to as $\omega1_{time=(t-1)}$), the drive system is able to approximately locate a new value of a first frequency point ω1. Once the commanded first frequency is achieved, the drive can transition back to a closed-loop operation or an adaptive open-loop operation and locate the exact value of ω1. Similarly, by driving a sensor at ω2, with the frequency obtained from the last measured value of ω2 (referred to as $\omega2_{time=(t-1)}$), the drive system is able to approximately locate a new value of a second frequency point ω2. Once the commanded second frequency is achieved, the drive can transition back to a closed-loop operation or an adaptive open-loop operation and locate the exact value of ω2.

As stated above, a purely closed-loop vibration can be used to initiate the vibration of the vibratory sensor. The vibration can then be switched to an open-loop vibration, or can be switched to using a combined open-loop and closed-loop vibration, wherein the open-loop part of an iteration greatly shortens an iteration time.

In addition, or alternatively, the meter electronics 20 can decide whether to employ open-loop vibrations, such as at each iteration, by checking various environmental factors. For example, the meter electronics 20 can use the open-loop vibration if the fluid being characterized is acceptably stable. The measured density of the fluid can be determined to be stable if it does not vary by more than a predetermined density tolerance over a predetermined time period.

Figure 6:
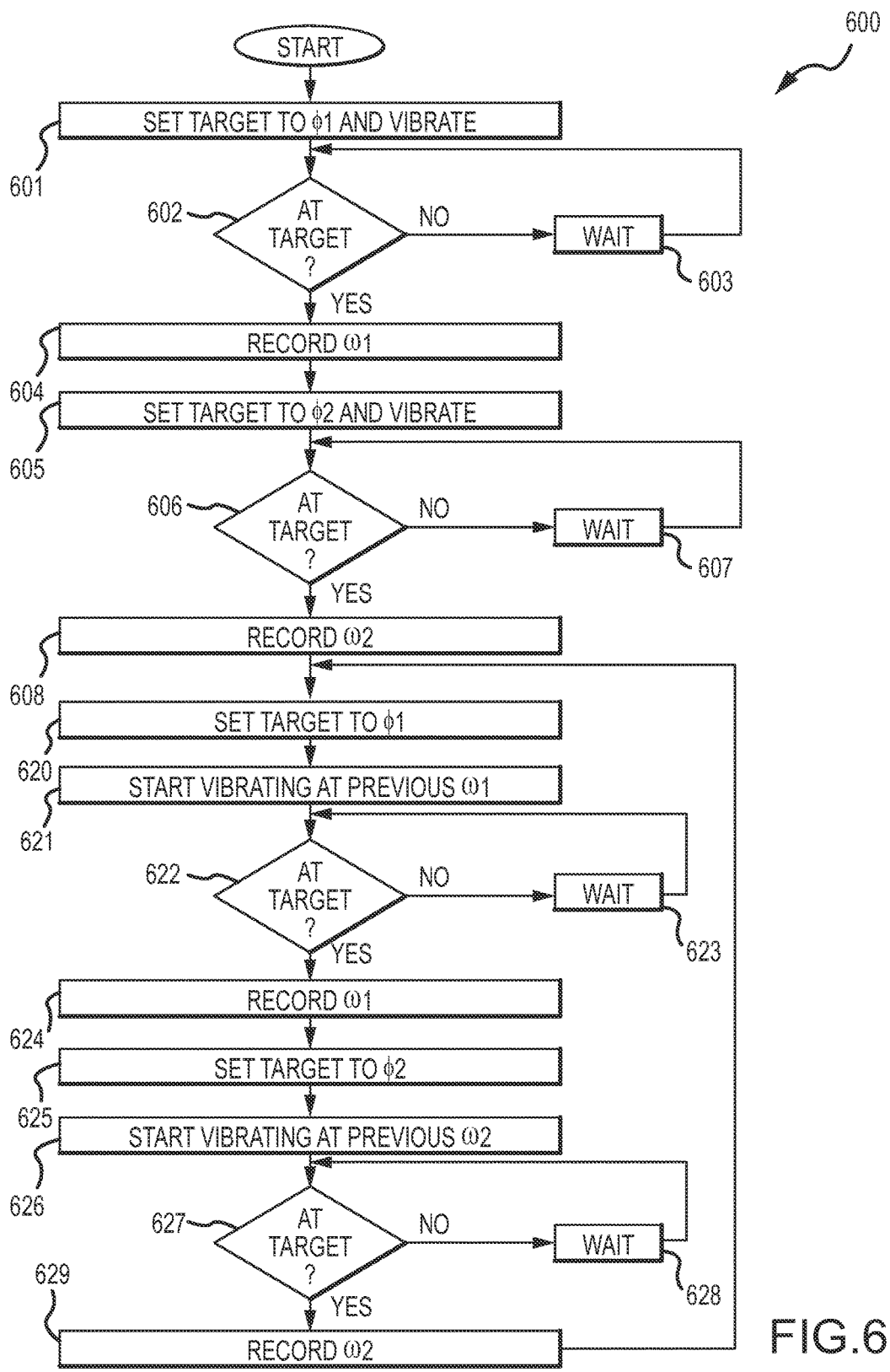
FIG. 6 is a flowchart of a method of varying vibration in the vibratory sensor according to an embodiment of the invention.

FIG. 6 is a flowchart 600 of a method of varying vibration in the vibratory sensor according to an embodiment of the invention. The closed-loop method steps 601-604 below determine the frequency of the first frequency point ω1 in a closed-loop manner, while the closed-loop method steps 605-608 determine the frequency of the second frequency point ω2 in a closed-loop manner. The open-loop method steps 620-624 below determine the frequency of the first frequency point ω1 in an open-loop manner, while the open-loop method steps 625-629 determine the frequency of the second frequency point ω2 in an open-loop manner.

In step 601, a vibration setpoint is set to a first target phase difference φ1 and the vibratory element is vibrated. The target phase difference is achieved by varying the frequency of the drive signal, starting from the current vibration frequency. The current vibration frequency is gradually changed, in a closed-loop manner and according to received feedback, such as feedback regarding the difference between a current phase difference and the target phase difference. The vibration frequency is incrementally ramped up or down from the current vibration frequency, depending on whether the phase difference is to be increased or decreased.

In step 602, the current phase difference is compared to the first target phase difference φ1. If the first target phase difference φ1 has been achieved, then the method proceeds to step 604. Otherwise, the method branches to step 603 until the first target phase difference φ1 is achieved.

In step 603, a wait is performed. Consequently, the method loops and waits until the vibration setpoint has been achieved. The vibratory sensor therefore waits for the actual vibration of the vibratory element to reach the vibration setpoint. Due to the closedloop drive operation, the vibratory element does not achieve vibration at the vibration setpoint until at least a known wait time has elapsed.

The wait may be for a fixed predetermined time or may vary in length. Environmental conditions may require a longer than expected time to achieve the target phase difference. The length of the wait may depend on various factors. The length of the wait may depend on a distance to the target phase difference from the initial phase difference. The length of the wait may depend on the physical characteristics of the vibratory element. The length of the wait may depend on the nature of the fluid being measured (including the density and/or viscosity of the fluid). The length of the wait may depend on the power available to the vibratory sensor. If the available electrical power is limited, the vibratory sensor may not be able to quickly ramp to the target phase difference and the corresponding frequency point ω1 or ω2.

In step 604, where the vibration setpoint has been achieved and the phase difference between the drive sensor signal and the pickoff sensor signal corresponds to the first phase difference φ1, then the corresponding first frequency point ω1 is recorded. The first frequency point ω1 comprises the vibration frequency that generates the first target phase difference φ1. The first frequency point ω1 comprises the frequency where the phase difference between the drive signal phase and the pickoff signal phase is about 135 degrees in some embodiments.

In step 605, the vibration setpoint is set to a second target phase difference φ2 and the vibratory element is vibrated from the current vibration frequency. The second target phase difference φ2 is achieved by varying the frequency of the drive signal, starting from the current vibration frequency. The current vibration frequency is gradually changed, in a closed-loop manner and according to received feedback, such as feedback regarding the difference between a current phase difference and the target phase difference. The vibration frequency is incrementally ramped up or down from the current vibration frequency, depending on whether the phase difference is to be increased or decreased. It should be understood that the starting vibration frequency is therefore the current vibration frequency, which comprises the vibration frequency obtained in step 604 above.

In step 606, the current phase difference is compared to the second target phase difference φ2. If the second target phase difference φ2 has been achieved, then the method proceeds to step 608. Otherwise, the method branches to step 607 until the second target phase difference φ2 is achieved.

In step 607, a wait is performed. Consequently, the method loops and waits until the vibration setpoint has been achieved. Due to the closedloop drive operation, the vibratory element does not achieve vibration at the vibration setpoint until at least a known wait time has elapsed, as previously discussed.

In step 608, where the vibration setpoint has been achieved and the phase difference between the drive sensor signal and the pickoff sensor signal corresponds to the second phase difference φ2, then the corresponding second frequency point ω2 is recorded. The second frequency point ω2 comprises the vibration frequency that generates the second target phase difference φ2. The second frequency point ω2 in some embodiments comprises the frequency where the phase difference between the drive signal phase and the pickoff signal phase is about 45 degrees in some embodiments.

The above closed-loop method steps 601-608 may comprise an initial or startup iteration for the vibratory flowmeter. The closed-loop method steps 601-608 in some embodiments may be used to generate initial values of the first and second frequency points ω1 and ω2. The closed-loop method steps 601-608 may be iterated one or more times before the method proceeds to the open-loop method steps 620-629, below.

In step 620, the vibration setpoint is set to the first target phase difference φ1.

In step 621, the vibratory sensor is vibrated at a commanded first frequency. Consequently, the vibration of the vibratory sensor transitions discontinuously from a current vibration frequency (i.e., the vibration frequency as it was immediately before this step) to the frequency value as given in the commanded first frequency. It should therefore be understood that the initial vibration frequency in this step is not the current vibration frequency. Vibration of the vibratory sensor therefore comprises an open-loop vibration process, at least for a period of time. As a result of vibrating in an open-loop manner, the resulting phase difference will immediately be close (or very close) to the first target phase difference φ1 when vibration commences at the commanded first frequency.

In some embodiments, the commanded first frequency comprises a previous-time first frequency point $\omega1_{time=(t-1)}$. The subscript [time=(t-1)] signifies that the first frequency point ω1 is from a previous time period (in the current iteration [time=t]). In some embodiments, the previous-time first frequency point $\omega1_{time=(t-1)}$ may comprise the first frequency point ω1 as obtained in a previous iteration of step 604 above, or as obtained in a previous iteration of step 624 below. However, it should be understood that the method is not limited to an immediately previous frequency value, and the value may be from an iteration farther back in time. Alternatively, the previous-time first frequency point $\omega1_{time=(t-1)}$ may comprise an ideal value that was previously determined or received and stored within the vibratory sensor, such as an expected frequency value for a predetermined fluid to be characterized.

It should be understood that after the open-loop vibration transition to the previous-time first frequency point $\omega1_{time=(t-1)}$, the vibration may then return to a closed-loop or adaptive open-loop vibration process. Feedback (or other or additional information) may then be employed to refine the vibration and zero in on the first target phase difference φ1.

In step 622, the current phase difference is compared to the first target phase difference φ1. If the first target phase difference φ1 has been achieved, then the method proceeds to step 624. Otherwise, the method branches to step 623 until the first target phase difference φ1 is achieved.

In step 623, a wait is performed. Consequently, the method loops and waits until the vibration setpoint has been achieved. The wait may be for a fixed predetermined time or may vary in length. The length of the wait may depend on various factors, such as the distance to the target phase difference from the initial phase difference, the physical characteristics of the vibratory element, the nature of the fluid being measured (including the density and/or viscosity of the fluid), and the power available to the vibratory sensor. However, the wait of step 623 will be significantly less than the wait length of step 603 above. Because step 621 vibrates the vibratory sensor in an open-loop manner, and starts with a frequency that will be close to the final frequency, the amount of time needed for the vibratory sensor to achieve the target phase difference is significantly reduced.

In step 624, where the vibration setpoint has been achieved and the phase difference between the drive sensor signal and the pickoff sensor signal corresponds to the first phase difference φ1, then the corresponding first frequency point ω1 is recorded. The first frequency point ω1 comprises the vibration frequency that generates the first target phase difference φ1. The first frequency point ω1 comprises the frequency where the phase difference between the drive signal phase and the pickoff signal phase is about 135 degrees in some embodiments.

The newly-determined first frequency point ω1 in some embodiments may be used as the previous-time first frequency point $\omega1_{time=(t-1)}$ in a future iteration (or iterations) of the open-loop method steps 620-624.

In step 625, the vibration setpoint is set to the second target phase difference φ2.

In step 626, the vibratory sensor is vibrated at a commanded second frequency. Consequently, the vibration of the vibratory sensor transitions discontinuously from a current vibration frequency (i.e., the vibration frequency as it was immediately before this step) to the frequency value as given in the commanded second frequency. It should therefore be understood that the initial vibration frequency in this step is not the current vibration frequency. Vibration of the vibratory sensor therefore comprises an open-loop vibration process, at least for a period of time. As a result of vibrating in an open-loop manner, the resulting phase difference will immediately be close (or very close) to the second target phase difference φ2 when vibration commences at the commanded second frequency.

In some embodiments, the commanded second frequency comprises a previous-time second frequency point $\omega 2_{time=(t-1)}$. The subscript [time=(t−1)] signifies that the second frequency point ω2 is from a previous time period (in the current iteration [time=t]). In some embodiments, the previous-time second frequency point $\omega 2_{time=(t-1)}$ may comprise the second frequency point ω2 as obtained in a previous iteration of step 608 above, or as obtained in a previous iteration of step 629 below. However, it should be understood that the method is not limited to an immediately previous frequency value, and the value may be from an iteration farther back in time. Alternatively, the previous-time second frequency point $\omega 2_{time=(t-1)}$ may comprise an ideal value that was previously determined or received and stored within the vibratory sensor, such as an expected frequency value for a predetermined fluid to be characterized.

It should be understood that after the open-loop vibration transition to the previous-time second frequency point $\omega 2_{time=(t-1)}$, the vibration may then return to a closed-loop or adaptive open-loop vibration process. Feedback (or other or additional information) may then be employed to refine the vibration and zero in on the second target phase difference φ2.

In step 627, the current phase difference is compared to the second target phase difference φ2. If the second target phase difference φ2 has been achieved, then the method proceeds to step 629. Otherwise, the method branches to step 628 until the second target phase difference φ2 is achieved.

In step 628, a wait is performed. Consequently, the method loops and waits until the vibration setpoint has been achieved. The wait may be for a fixed predetermined time or may vary in length. The length of the wait may depend on various factors, such as the distance to the target phase difference from the initial phase difference, the physical characteristics of the vibratory element, the nature of the fluid being measured (including the density and/or viscosity of the fluid), and the power available to the vibratory sensor. However, the wait of step 628 will be significantly less than the wait length of step 607 above. Because step 626 vibrates the vibratory sensor in an open-loop manner, and starts with a frequency that will be close to the final frequency, the amount of time needed for the vibratory sensor to achieve the target phase difference is significantly reduced.

In step 629, where the vibration setpoint has been achieved and the phase difference between the drive sensor signal and the pickoff sensor signal corresponds to the second phase difference φ2, then the corresponding second frequency point ω2 is recorded. The second vibration frequency point ω2 comprises the vibration frequency that generates the second target phase difference φ2. The second frequency point ω2 comprises the frequency where the phase difference between the drive signal phase and the pickoff signal phase is about 45 degrees in some embodiments.

The newly-determined second frequency point ω2 in some embodiments may be used as the previous-time second frequency point $\omega 2_{time=(t-1)}$ in a future iteration (or iterations) of the open-loop method steps 625-629.

The vibratory sensor 5 according to any of the embodiments reacts faster changes in the fluid being characterized using the open-loop operation.

It should be understood that the closed-loop method steps 601-608 may comprise an initial or startup process, wherein the closed-loop method steps 601-608 are executed at least once. The closed-loop method steps 601-608 may be not executed during normal operation or after the initial or startup process. In some embodiments, the open-loop method steps 620-629 may be iteratively executed and the closed-loop method steps 601-608 are executed merely to derive initial values of the frequency points ω1 and ω2. Alternatively, in some embodiments the steps closed-loop method 601-608 may be executed periodically or intermittently, including on an as-needed basis, for example.

In an alternative embodiment, the first and second frequency points ω1 and ω2 may be found by measuring the power of the vibration signal and determining the first and second frequency points ω1 and ω2 from the points of half-power in the vibration signal. It should be understood that the frequency points found by measuring power may be approximately the same as the frequency points found by monitoring the phase difference, but may not be exactly the same.

Figure 7:
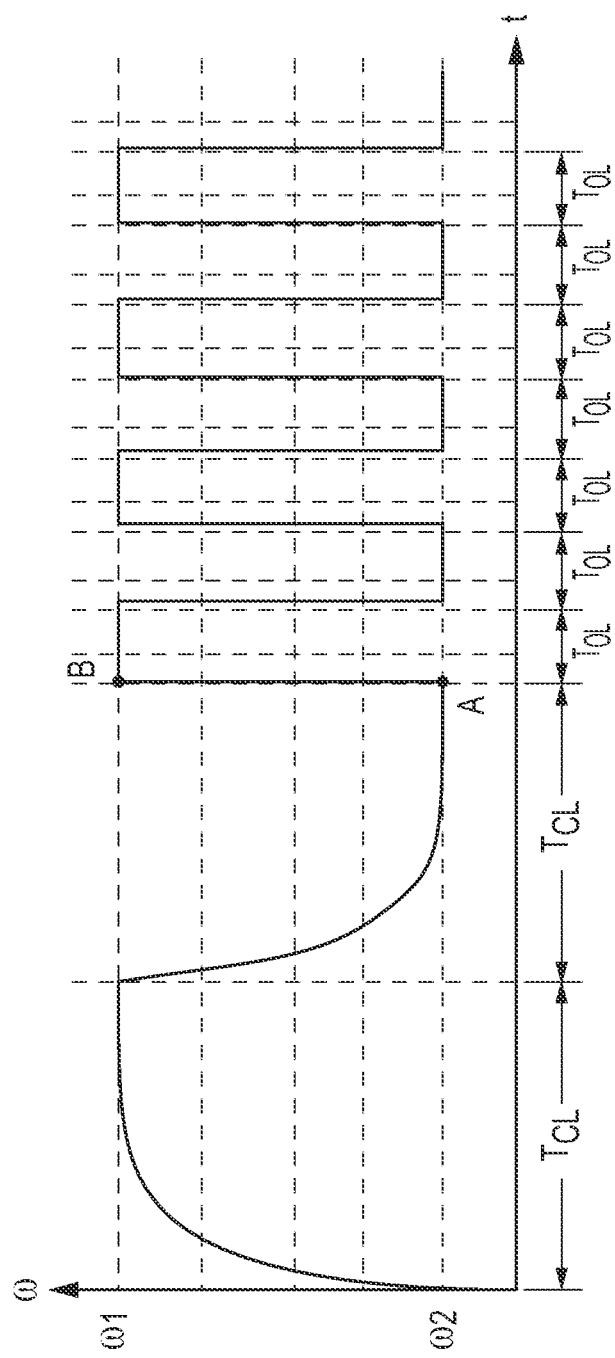
FIG. 7 is a graph of the combined closed-loop and open-loop vibration response of the vibratory sensor.

FIG. 7 is a graph of the combined closed-loop and open-loop vibration responses of the vibratory sensor of FIGS. 4-5 and/or the combined closed-loop and open-loop vibration responses of the method of FIG. 6. The vertical axis represents vibration frequency (ω) and the horizontal axis represents time (t). It can be seen that the prior art vibratory sensor is alternatingly vibrated at the first frequency point ω1 and then at the second frequency point ω2, wherein this pattern is iteratively repeated. Although the frequency points ω1 and ω2 are shown as being constant, it should be understood that the first and second frequency points ω1 and ω2 may change due to changes in the fluid being characterized by the vibratory sensor, for example. In addition, the first and second frequency points ω1 and ω2 may change due to changes in environmental conditions, such as due to changes in temperature and/or pressure, for example.

The first two vibration occurrences span two closed-loop time periods $T_{CL}$. The first two vibration occurrences comprise vibration in a closed-loop manner, wherein vibration commences at the frequency point ω1 and the vibration is smoothly and continuously varied until the vibration achieves the frequency point ω2 or the vibration commences at the frequency point ω2 and the vibration is smoothly and continuously varied until the vibration achieves the frequency point ω1. Due to the closed-loop vibration in the first two vibration occurrences, it can be seen that the actual vibration frequency changes smoothly and continuously, but slowly. Each change in drive frequency requires a closed-loop time period $T_{CL}$ to accomplish, due to the feedback used to achieve the target phase difference. As a result, the prior art vibratory tine sensor cannot measure rapid changes in the frequency points ω1 and ω2, and therefore cannot measure rapid changes in density and/or viscosity of the fluid to be characterized.

The subsequent seven vibration occurrences shown in the figure span open-loop time periods $T_{CL}$. The subsequent seven vibration occurrences comprise vibration in an open-loop manner, wherein vibration commences at a commanded target vibration and the vibration discontinuously transitions from a previous vibration to the commanded target vibration. For example, at the beginning of the first open-loop time period $T_{CL}$ (point A on the graph), where the vibration frequency is currently the second frequency point ω2, the vibration nevertheless transitions abruptly and discontinuously to the first frequency point ω1 (point B).

As stated above, a purely closed-loop vibration can be used to initiate vibration. The vibration can then switch to using a purely open-loop vibration, or can switch to using a combined open-loop and closed-loop vibration, wherein the open-loop part of an iteration greatly shortens an iteration time.

In addition, or alternatively, the meter electronics 20 can decide whether to employ open-loop vibration, such as at each iteration, by checking various environmental factors. For example, the meter electronics 20 can use the open-loop vibration if the fluid being characterized is substantially stable. The measured density of the fluid can be determined to be stable if it does not vary by more than a predetermined density tolerance over a predetermined time period.

The detailed descriptions of the above embodiments are not exhaustive descriptions of all embodiments contemplated by the inventors to be within the scope of the invention. Indeed, persons skilled in the art will recognize that certain elements of the above-described embodiments may variously be combined or eliminated to create further embodiments, and such further embodiments fall within the scope and teachings of the invention. It will also be apparent to those of ordinary skill in the art that the above-described embodiments may be combined in whole or in part to create additional embodiments within the scope and teachings of the invention. Accordingly, the scope of the invention should be determined from the following claims.

What is claimed is:

1. A method of varying vibration in a vibratory sensor, with the method comprising:

vibrating a vibratory element of a vibratory sensor commencing at a commanded first frequency and in an open-loop manner to achieve a first target phase difference$\phi 1$ for a fluid being characterized and determining a corresponding first frequency point $\omega 1$;

vibrating the vibratory element commencing at a commanded second frequency and in the open-loop manner to achieve a second target phase difference $\phi 2$ and determining a corresponding second frequency point $\omega 2$; and determining a viscosity of the fluid being characterized using the first frequency point $\omega 1$ and the second frequency point $\omega 2$ by a meter electronic unit; wherein the steps of: vibrating the vibratory element in a closed-loop manner to achieve the first target phase difference $\phi 1$ for the fluid being characterized and determining a corresponding first frequency point $\omega 1$, with the vibrating commencing at the current vibration frequency; and vibrating the vibratory element in the closed-loop manner to achieve the second target phase difference $\phi 2$ for the fluid being characterized and determining a corresponding second frequency point $\omega 2$, with the vibrating commencing at the current vibration frequency.

2. The method of claim 1, iteratively performing the vibrating and determining steps.

3. The method of claim 1, with the commanded first frequency comprising a previous-time first frequency point $\omega 1_{time=(t-1)}$) and with the commanded second frequency comprising a previous-time second frequency $\omega 2_{time=(t-1)}$).

4. The method of claim 1, with vibrating the vibratory element in the open-loop manner comprising:

setting a vibration setpoint to the first target phase difference $\phi 1$;

vibrating the vibratory element in the open-loop manner and at the commanded first frequency;

comparing a current first phase difference to the first target phase difference $\phi 1$ and waiting until the current first phase difference is substantially equal to the first target phase difference $\phi 1$;

if the current first phase difference is equal to the first target phase difference $\phi 1$, then recording the corresponding first frequency point $\omega 1$, wherein achieving the first target phase difference $\phi 1$ generates the first frequency point $\omega 1$ in the vibratory element;

setting the vibration setpoint to the second target phase difference $\phi 2$;

vibrating the vibratory element in the open-loop manner and at the commanded second frequency;

comparing a current second phase difference to the second target phase difference $\phi 2$ and waiting until the current second phase difference is substantially equal to the second target phase difference $\phi 2$; and if the current second phase difference is equal to the second target phase difference $\phi 2$, then recording the corresponding second frequency point $\omega 2$, wherein achieving the second target phase difference $\phi 2$ generates the second frequency point $\omega 2$ in the vibratory element.

5. The method of claim 1, wherein the method selects the open-loop operation if the fluid being characterized is substantially stable.

6. The method of claim 1, with the vibrating steps comprising:

vibrating the vibratory element commencing at the commanded first frequency and in the open-loop manner to approximate the first target phase difference $\phi 1$ for a fluid being characterized;

vibrating the vibratory element in a closed-loop manner to achieve the first target phase difference $\phi 1$ and determining a corresponding first frequency point $\omega 1$;

vibrating the vibratory element commencing at the commanded second frequency and in the open-loop manner to approximate the second target phase difference $\phi 2$ for the fluid being characterized;

vibrating the vibratory element in the closed-loop manner to achieve the second target phase difference $\phi 2$ and determining a corresponding second frequency point $\omega 2$; and determining a viscosity of the fluid being characterized using the first frequency point $\omega 1$ and the second frequency point $\omega 2$.

7. The method of claim 1, with the vibratory sensor comprising a vibratory tine sensor and with the vibratory element comprising a tuning fork structure.

* * * * *